United States Patent [19]

Godbey et al.

[11] Patent Number: 5,264,219
[45] Date of Patent: Nov. 23, 1993

[54] TRANSDERMAL DRUG DELIVERY BACKING

[75] Inventors: Kristin J. Godbey; Philip G. Martin, both of Ramsey, Minn.

[73] Assignee: Minnesota Mining and Manufacturing Company, St. Paul, Minn.

[21] Appl. No.: 926,910

[22] Filed: Aug. 7, 1992

[51] Int. Cl.$^5$ .............................................. A61F 13/00
[52] U.S. Cl. ..................................................... 424/449
[58] Field of Search ........................ 424/449, 448, 443

[56] References Cited

U.S. PATENT DOCUMENTS

| | | | |
|---|---|---|---|
| 4,804,714 | 2/1989 | Olivo | 525/240 |
| 4,900,554 | 2/1990 | Yanagibashi et al. | 424/449 |
| 4,994,278 | 2/1991 | Sablotsky et al. | 424/449 |
| 5,000,956 | 3/1991 | Amkraw et al. | 424/449 |
| 5,011,891 | 4/1991 | Spenadel et al. | 525/211 |
| 5,023,084 | 6/1991 | Chien et al. | 424/449 |

FOREIGN PATENT DOCUMENTS

0405793A2  1/1991  European Pat. Off. .

*Primary Examiner*—Thurman K. Page
*Assistant Examiner*—Leon R. Horne
*Attorney, Agent, or Firm*—Gary L. Griswold; Walter N. Kirn; Douglas E. Reedich

[57] ABSTRACT

Polymer blends containing a very low density polyethylene copolymer of ethylene and 1-butene, 1-hexene, or 1-octene and about 15 to about 600 parts by weight of a linear low density polyethylene copolymer of ethylene and 1-octene, based on 100 parts by weight of the very low density polyethylene copolymer.

1 Claim, No Drawings

TRANSDERMAL DRUG DELIVERY BACKING

BACKGROUND OF THE INVENTION

1. Technical Field

This invention relates to polymer blends, and more particularly it relates to blends of polyethylene copolymers. In another aspect this invention relates to transdermal drug delivery devices and to backings for use in such devices. This invention also relates to extruded films.

2. Description of the Related Art

Transdermal drug delivery is an increasingly important method of drug administration. Transdermal drug delivery devices typically involve a carrier (such as a liquid, gel, or solid matrix, or a pressure sensitive adhesive) into which the drug to be delivered is incorporated. The drug-containing carrier is then placed on the skin and the drug, along with any adjuvants and excipients, is delivered to the skin.

Typically the portions of the carrier that are not in contact with the skin are covered by a backing. The backing serves to protect the carrier (and the components contained in the carrier, including the drug) from the environment and prevents loss of the ingredients of the drug delivery device to the environment. Because hydration of the stratum corneum is known to enhance transport of certain drugs across the skin, it is sometimes desirable that the backing have a relatively low moisture vapor transmission rate in order to retain moisture at the site covered by the drug delivery device. In order to maintain the health of the covered skin during long term wear (e.g., for periods in excess of a day) by allowing the skin to breath, it is also desirable that the backing have relatively high permeability to oxygen. Further, as the backing is in contact with the components of the carrier, including the drug and any adjuvants and excipients, it is important that the backing be stable to such components in order that the backing retain structural integrity, tensile strength, and conformability to the skin. It is also important that the backing not absorb drug or other excipients from the carrier. In connection with the preparation of certain reservoir-type transdermal drug delivery devices, it is also desirable for the backing to be heat sealable at a relatively low temperature to itself and to a variety of other polymeric substrates.

Backing materials that have found use in transdermal drug delivery devices include metal foils, metalized plastic films, and single layered and multilayered polymeric films. Deficiencies of these backings that are occasionally manifest include delamination of multilayered polymeric films, oxygen impermeability of metal foils, metalized plastic films, and certain polymeric films, instability of certain polymeric materials to the components of the carrier, and absorption of components from the carrier by certain polymeric materials. Also, it is known that certain polymeric materials are difficult to handle and process into suitable films.

SUMMARY OF THE INVENTION

This invention provides a polymer blend, comprising:
(i) a very low density polyethylene random copolymer comprising about 80 to about 95 mole percent ethylene and a total of about 5 to about 20 mole percent of a comonomer selected from the group consisting of 1-butene, 1-hexene, 1-octene, and a combination of two or more thereof; and (ii) about 15 to about 600 parts by weight, based on 100 parts by weight of the very low density polyethylene, of a linear low density polyethylene random copolymer comprising about 92 to about 98 mole percent ethylene and about 2 to about 8 mole percent 1-octene.

This invention also provides a flexible sheet material, comprising a polymer blend as described above in the form of a film about 10 to about 300 $\mu$m thick. Such a sheet material finds particular utility in the form of a flexible backing for use in a transdermal drug delivery device.

This invention also provides a transdermal drug delivery device comprising: a flexible backing as described above, and a carrier comprising a therapeutically effective amount of a drug, wherein the carrier bears the backing on at least part of one surface of the carrier.

The polymer blends and flexible sheet materials of the invention avoid the above mentioned deficiencies of the various prior art backing materials. For example they can be used to avoid processing difficulties that can arise when using either component of the blend in the absence of the other component. Further they are permeable to oxygen, stable to various common components of transdermal drug delivery devices, strong, conformable, and they do not absorb significant amounts of certain common elements of transdermal carriers. The polymer blends of the invention are suitable for use as single layer backings, which avoid the possibility of delamination that can exist with multilayer backings. While the component copolymers of the blends are translucent or hazy, the blends of the invention are clear, colorless, and transparent to visible light, rendering them suitable for use in fashioning a visually unobtrusive transdermal drug delivery device. Further, sheet materials fashioned from the blends of the invention can be heat sealed at a relatively low temperature.

DETAILED DESCRIPTION OF THE INVENTION

The copolymer components of the polymer blends of the invention are defined herein in terms of the mole percent of the comonomers present in the copolymers. The mole percentages set forth herein are the result of determinations involving nuclear magnetic resonance. Weight average molecular weights recited herein were determined by gel permeation chromatography. Those skilled in the art will recognize the level of precision of such methods.

The term "very low density polyethylene" as used herein is intended to be synonymous with the term "ultra low density polyethylene".

The polymer blends of the invention comprise a very low density polyethylene copolymer (VLDPE). This copolymer preferably comprises about 80 to about 95 mole percent ethylene and a total of about 5 to about 20 mole percent of a comonomer selected from the group consisting of 1-butene, 1-hexene, 1-octene, and a combination of two or more thereof. A preferred VLDPE is FLEXOMER TM DFDA 1137 NT7 polyolefin (commercially available from Union Carbide), a material comprising a copolymer of about 93 mole percent ethylene and about 7 mole percent 1-butene. This copolymer is said to have a density of 0.905 g/cm$^3$ (ASTM D-1505), a weight average molecular weight of about 240,000, and a melt index of 1.0 g/10 min (ASTM D-

1238). FLEXOMER ™ DFDA 1138 NT polyolefin (commercially available from Union Carbide), a material comprising a copolymer of about 91 mole percent ethylene and about 9 mole percent 1-butene and having a density of 0.900 g/cm$^3$ (ASTM D-1505), a weight average molecular weight of about 260,000, and a melt index of 0.4 g/10 min (ASTM D-1238) is also suitable.

Other exemplary VLDPEs suitable for use in the polymer blends of the invention include:

FLEXOMER ™ GERS 1085 NT polyolefin (Union Carbide), comprising a copolymer of about 85 mole percent ethylene and about 15 mole percent 1-butene, having a density of 0.884 g/cm$^3$ (ASTM D-1505), a weight average molecular weight of about 250,000, and a melt index of about 0.8 g/10 min (ASTM D-1238);

FLEXOMER ™ DEFD 1491 NT7 polyolefin (Union Carbide), comprising a copolymer of about 92 mole percent ethylene and about 8 mole percent 1-butene, having a density of 0.900 g/cm$^3$ (ASTM D-1505), a weight average molecular weight of about 220,000, and a melt index of about 1.0 g/10 min (ASTM D-1238);

FLEXOMER ™ 9020 NT7 polyolefin (Union Carbide), comprising a copolymer of about 93 mole percent ethylene and about 7 mole percent 1-butene, having a density of 0.905 g/cm$^3$ (ASTM D-1505), a weight average molecular weight of about 200,000, and a melt index of about 0.85 g/10 min (ASTM D-1238);

FLEXOMER ™ DFDA 1164 NT7 polyolefin (Union Carbide), comprising a copolymer of about 94 mole percent ethylene, about 1 mole percent 1-butene, and about 5 mole percent 1-hexene, having a density of about 0.910 g/cm$^3$ (ASTM D 1505), a weight average molecular weight of about 240,000, and a melt index of about 1.0 g/10 min (ASTM D 1238);

FLEXOMER ™ 9042 NT polyolefin (Union Carbide), comprising a copolymer of about 90 mole percent ethylene and about 10 mole percent 1-butene, having a density of 0.900 g/cm$^3$ (ASTM D-1505), a weight average molecular weight of about 135,000, and a melt index of about 5.0 g/10 min (ASTM D-1238);

FLEXOMER ™ DFDA 9063 polyolefin (Union Carbide), comprising a copolymer of about 93 mole percent ethylene and about 7 mole percent 1-butene, having a density of 0.910 g/cm$^3$ (ASTM D-1505), a weight average molecular weight of about 270,000, and a melt index of about 0.5 g/10 min (ASTM D-1238);

ATTANE ™ 4203 polyolefin (Dow), comprising a copolymer of about 90 mole percent ethylene and about 10 mole percent 1-octene, having a weight average molecular weight of about 220,000;

ATTANE ™ 4802 polyolefin (Dow), comprising a copolymer of about 95 mole percent ethylene and about 5 mole percent 1-octene, having a density of 0.912 g/cm$^3$ (ASTM D-1505), a weight average molecular weight of about 290,000, and a melt index of about 3.3 g/10 min (ASTM D-1238).

Blends of two or more of the above-described VLDPEs in any proportion are also suitable for use as the VLDPE component of a polymer blend of the invention.

The VLDPEs suitable for use in the polymer blends of the invention generally have a density in the range of about 0.87 to about 0.93 g/cm$^3$, preferably about 0.90 to about 0.92 g/cm$^3$, and a weight average molecular weight of about 100,000 to about 300,000, preferably about 130,000 to about 270,000. The VLDPEs also preferably have a polydispersity of about 3.5 to about 6.

The polymer blends of the invention also comprise a linear low density polyethylene copolymer (LLDPE). This copolymer preferably comprises about 92 to about 98 mole percent ethylene and about 2 to about 8 mole percent 1-octene. Exemplary suitable LLDPEs include DOWLEX ™ 2503 and DOWLEX ™ 6806 polyolefin (Dow), linear low density polyethylenes having a density of about 0.930 g/cm$^3$, a melt index of 105 g/10 min, and a weight average molecular weight of about 60,000. The LLDPE also preferably has a polydispersity between about 2 to about 3.

The LLDPEs suitable for use in the polymer blends of the invention generally have a density in the range of about 0.92 to about 0.94 g/cm$^3$, preferably about 0.93 g/cm$^3$, and a weight average molecular weight of about 50,000 to about 70,000, preferably about 60,000.

Blends of two or more of the above-described LLDPEs in any proportion are also suitable for use as the LLDPE component of a polymer blend of the invention.

The LLDPE component is preferably present in an amount of about 15 parts by weight to about 600 parts by weight based on 100 parts by weight of the VLDPE. More preferably the blends comprise about 15 to about 100 parts by weight LLDPE, and most preferably about 50 to about 60 parts by weight LLDPE, based on 100 parts by weight VLDPE.

The polymer blends of the invention, and the sheet materials and backings of the invention, can also contain suitable amounts of conventional polymer additives, such as processing aids, pigments, and lubricants. The amount that constitutes a suitable amount of such components can be readily determined by those skilled in the art.

The individual copolymer components of the polymer blends of the invention are commercially available as set forth above, and furthermore can be readily prepared using methods well known to those skilled in the art. In order to prepare the polymer blends of the invention, the selected components can be blended using melt processing techniques well known to those skilled in the art. A preferred method of preparing a polymer blend of the invention involves combining preselected amounts of the component copolymers in the form of dry pellets to form a dry polymer blend. The dry blend is then fed into a conventional extruder (e.g., a single screw extruder) operated at an appropriate temperature. As the mix passes through the extruder the component copolymers are melted and blended to form the polymer blend.

The polymer blend can be processed into useful articles of the invention (such as flexible sheet materials and components for transdermal drug delivery devices) by using conventional polymer processing techniques, such as molding, blowing, and extruding. In fashioning a flexible sheet material of the invention, it is preferred to extrude the polymer blend from an extruder (e.g., a single screw extruder) through an appropriate die and onto a casting roll in order to form a sheet material of the desired thickness. The preferred thickness of the sheet materials and transdermal backings of the invention is about 10 to about 130 μm, most preferably about 70 to about 80 μm.

A transdermal drug delivery device can be prepared from a flexible sheet material of the invention by using conventional methods to apply an appropriate carrier to the flexible sheet material. An appropriate carrier containing a therapeutically effective amount of a drug and any excipients and adjuvants can be prepared by methods well known to those skilled in the art. The term "carrier" as used herein refers generally to any element suitable for containing a drug and releasing the drug to the skin. A carrier generally has a surface adapted to be applied to the skin and an opposing surface adapted to be applied to a backing. Pressure sensitive adhesives are but one type of carrier.

Exemplary drugs that can be included in the carrier include any substance capable of local or systemic effect when administered to the skin, such as clonidine, estradiol, nicotine, nitroglycerine, and scopolamine, all of which are commercially available in the form of transdermal devices. Others include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); cardioactive products such as atriopeptides; proteinaceous products (e.g., insulin); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

Certain adjuvants and excipients are often used as components of transdermal drug delivery devices. Fatty acids (such as isostearic acid, oleic acid, and linoleic acid) sometimes find use, as do fatty acid esters (such as ethyl oleate and isopropyl myristate). Solvents such as ethanol are also sometimes used. Selection of such adjuvants and excipients, however, is dependent on the drug to be delivered and the type of carrier employed.

The polymer blends of the invention are suitable for use as packaging films. They are particularly suitable for use as backings in transdermal drug delivery devices. Those skilled in the art will recognize that suitability of such a backing is a function of several different properties and is not represented by any single test result, property, or feature. The Examples below, however, indicate that the polymer blends of the invention can be fashioned into sheet materials that generally have a relatively high barrier to moisture, a relatively low barrier to oxygen, are stable to certain common excipients, and have good tensile strength and elongation at break. High tensile strength and high percentage elongation at break are desired in a flexible film in order to avoid breakage during handling and processing of the film. Also, percent elongation at break serves as an indication of flexibility and conformability of a film to the skin.

Certain of the blends of the invention were tested and found not to contain unsuitable amounts of diffusible cytotoxic components or leachable toxic components. Certain of the blends of the invention were also tested and not found to be unduly irritating to skin. Further, certain of the blends of the invention have been found to be heat sealable to themselves or to other polymeric materials at relatively low temperatures.

The test methods set forth below are used in connection with the Examples that follow.

Moisture Vapor Transmission Rate (MVTR) was determined using ASTM F 1249-90.

Tensile Strength (peak) and the Percentage Elongation at Break were determined using ASTM D 882-90 Test Method A, rate of grip separation of 51 cm/min, initial distance between grips of 5 cm, initial strain rate of 25 cm/cm min.

The effect on tensile strength and percentage elongation at break produced by exposure of a flexible sheet material of the invention to various materials that are used as adjuvants or excipients in transdermal drug delivery (e.g., skin penetration enhancers) was determined as follows. Samples (2.5 cm by 10 cm; ten cut with their longer axis parallel to the axis of the casting roll, and ten cut with their longer axis perpendicular to the axis of the casting roll) were cut from the sheet material. Each sample was folded along its longer axis into an "S" shape and then placed on edge in a 60 mL vial. Approximately 30 mL of the selected material (ethanol, oleic acid, or isopropyl myristate) was added to each vial in order to completely cover the sample. The vials were capped then placed in an oven at 38° C. for one week. The vials were removed from the oven and allowed to cool to room temperature. Each sample was removed from the vial with tweezers and blotted between multiple sheets of paper towel. The tensile strength and percentage elongation at break of each sample was then determined using the test procedures referenced above.

EXAMPLE 1

FLEXOMER TM resin DFDA-1137-NT (1300 g; available from Union Carbide) was dry blended with 700 g of DOWLEX TM 6806 resin (available from Dow Chemical Company). The blend was melt processed in a BERLYN TM 2 inch (5 cm) single screw extruder with a length:diameter ratio of 32:1 and a screw equipped with a Maddock mixer. Zone temperatures were set as follows: Zone 1 at 138° C.; Zone 2 at 178° C.; Zone 3 at 233° C.; Zones 4–7 at 249° C. The polymer melt was passed via a neck tube (249° C.) to a 18 inch (46 cm) single layer EDI die (232° C.). The sheet material was cast on a chrome roll maintained at a temperature of 16° C. The line speed was 5.2 m/min. The casting roll was nipped to produce a matte finish on the sheet material. After casting, the sheet material was collected on standard web handling equipment. The sheet material had a thickness of 75 μm, a MVTR of 6.6 g/m$^2$/24 hours, a tensile strength at peak of 1.07 Kg per cm of width and a percentage elongation at break of 645.

EXAMPLES 2–36

Using the general method of Example 1, sheet materials were prepared having the compositions shown in Table 1. Films were variously cast with the casting roll nipped or unnipped. An unnipped configuration produces a clear colorless sheet material and a nipped roll produces a sheet material with a matte finish. In Table 1, in all instances the LLDPE is DOWLEX TM 6806 resin, the thickness is in μm, the MVTR is in g/m$^2$/24 hours, and the tensile strength at peak (TS) is in Kg per cm of width. The absence of an entry indicates that the particular value was not measured. Percentages are given as weight percent of each component based on the total weight of the polymer blend. The chemical compositions of the materials designated in the TABLE are set forth in the specification above.

EXAMPLES 37–40

Several opaque pigmented films were prepared by dry blending FLEXOMER DFDA-1137-NT resin, DOWLEX 6806 resin and Spectrum #1065306E pigment and then proceeding according to the general method of Example 1. The compositions and properties of these films are shown in Table 2. In all examples the VLDPE is FLEXOMER DFDA-1137-NT resin the LLDPE is DOWLEX 6806 resin and the pigment is Spectrum #1055306E. All films had a caliper of 75 microns. The MVTR value is in g/m$^2$/24 hours and the tensile strength at peak is in Kg per cm of width. Percentages are given in weight percent of each component based on the total weight of polymer blend.

TABLE 2

| Ex | % VLDPE | % LLDPE | % Pigment | MVTR | TS | % Elong |
|---|---|---|---|---|---|---|
| 37 | 62 | 33 | 5 | 6.7 | 1.05 | 632 |
| 38 | 59 | 32 | 10 |  | 1.25 | 734 |
| 39 | 52 | 28 | 20 | 6.6 | 1.29 | 795 |
| 40 | 55 | 30 | 15 | 7.5 | 1.25 | 710 |

Using the test method described above, the effect of exposure to various materials on the tensile strength and percentage elongation at break of films of the invention was determined. The results are shown in Table 3. The tensile strength at peak values are in Kg per cm of width.

TABLE 1

| Ex | VLDPE | % LLDPE | Thickness (μm) | MVTR (g/m$^2$/24 h) | TS (kg/cm width) | % Elong |
|---|---|---|---|---|---|---|
| 2 | 85% DEFD-9042-NT | 15 | 142 | 6.3 | 1.18 | 1160 |
| 3 | 85% GERS-1085-NT | 15 | 87 | 18.2 | 0.62 | 1145 |
| 4 | 50% DFDA-1137-NT | 50 | 65 | 7.0 | 0.57 | 920 |
| 5 | 65% DFDA-1137-NT | 35 | 50 | 11.3 | 0.50 | 925 |
| 6 | 85% DFDA-1137-NT | 15 | 50 |  | 0.46 | 620 |
| 7 | 85% DFDA-1137-NT | 15 | 65 | 9.9 | 0.32 | 655 |
| 8 | 85% DEFD-9042-NT | 15 | 60 | 15.7 | 0.38 | 655 |
| 9 | 15% DFDA-1137-NT | 85 | 75 |  | 5.4 | 0.93 | 583 |
| 10 | 35% DFDA-1137-NT | 65 | 75 |  | 6.5 | 0.89 | 629 |
| 11 | 85% Attane 4203 | 15 | 75 | 6.3 | 2.30 | 826 |
| 12 | 65% Attane 4802 | 35 | 75 | 6.6 | 1.50 | 854 |
| 13 | 65% Attane 4802 | 35 | 75 |  | 1.23 | 893 |
| 14 | 50% Attane 4802 | 50 | 75 |  | 1.04 | 850 |
| 15 | 35% Attane 4802 | 65 | 75 |  | 0.98 | 683 |
| 16 | 35% Attane 4802 | 65 | 75 |  | 0.98 | 846 |
| 17 | 15% DFDA 9063 | 85 | 75 |  | 1.09 | 968 |
| 18 | 15% DFDA 9063 | 85 | 75 |  | 0.95 | >1000 |
| 19 | 35% DFDA 9063 | 65 | 75 |  | 1.27 | 935 |
| 20 | 35% DFDA 9063 | 65 | 75 |  | 1.39 | 931 |
| 21 | 50% DFDA 9063 | 50 | 75 |  | 1.55 | 903 |
| 22 | 50% DFDA 9063 | 50 | 75 |  | 1.39 | 916 |
| 23 | 65% DFDA 9063 | 35 | 75 |  | 1.89 | 815 |
| 24 | 65% DFDA 9063 | 35 | 75 |  | 1.68 | 918 |
| 25 | 65% DFDA 9020 | 35 | 75 |  | 1.70 | 860 |
| 26 | 50% DFDA 9020 | 50 | 75 |  | 1.21 | 787 |
| 27 | 50% DFDA 9020 | 50 | 75 |  | 1.39 | 961 |
| 28 | 85% Attane 4803 | 15 | 75 | 10.4 | 2.39 | 839 |
| 29 | 65% Attane 4803 | 35 | 75 | 9.8 | 1.93 | 865 |
| 30 | 65% Attane 4803 | 35 | 75 |  | 1.18 | 742 |
| 31 | 50% Attane 4803 | 50 | 75 |  | 1.52 | 852 |
| 32 | 35% Attane 4803 | 65 | 75 |  | 1.38 | 818 |
| 33 | 35% Attane 4803 | 65 | 75 |  | 0.91 | 791 |
| 34 | 15% Attane 4803 | 85 | 75 |  | 0.95 | 767 |
| 35 | 15% DFDA 9063 | 85 | 75 |  | 1.70 | 793 |
| 36 | 85% DFDA 9020 | 15 | 75 |  | 2.11 | 895 |
| C1 | 0% DFDA 9063 | 100 | 75 | 5.4 | 0.73 | 484 |
| C2 | 100% DFDA-1137-NT | 0 | 37 | 10.7 | 0.41 | 370 |
| C3 | 100% Attane 4203 | 0 | 75 | 8.9 | 1.57 | 697 |
| C4 | 100% Attane 4802 | 0 | 75 | 10.0 | 2.27 | 805 |
| C5 | 100% DFDA 9020 | 0 | 75 |  | 1.98 | 888 |

TABLE 3

| Ex | Initial TS | Initial % Elon | Ethanol TS | Ethanol % Elon | Oleic Acid TS | Oleic Acid % Elon | Isopropyl Myristate TS | Isopropyl Myristate % Elon |
|---|---|---|---|---|---|---|---|---|
| 1 | 1.07 | 645 | 1.34 | 772 | 1.66 | 973 | 1.52 | 946 |
| 2 | 1.18 | 1160 | 1.18 | 1170 | | | | |
| 3 | 0.62 | 1145 | 0.45 | 980 | 0.21 | 525 | | |
| 4 | 0.57 | 920 | 0.50 | 930 | 0.48 | 985 | 0.46 | 1000 |
| 5 | 0.50 | 925 | 0.48 | 905 | 0.34 | 800 | 0.34 | 810 |
| 6 | 0.46 | 620 | 0.46 | 730 | 0.64 | 780 | 0.70 | 940 |
| 7 | 0.32 | 655 | 0.36 | 715 | 0.30 | 628 | | |
| 8 | 0.38 | 655 | 0.32 | 560 | 0.34 | 690 | 0.38 | 770 |
| 9 | 0.73 | 484 | 0.80 | 487 | 0.77 | 408 | 0.71 | 364 |
| 10 | 0.89 | 629 | 1.05 | 786 | 1.09 | 889 | 1.09 | 906 |
| 12 | 1.50 | 854 | 1.45 | 861 | 1.09 | 755 | 1.02 | 818 |
| 13 | 1.23 | 893 | 0.98 | 754 | | | 0.82 | 827 |
| 23 | 1.89 | 815 | 1.57 | 770 | 1.70 | 857 | 1.21 | 719 |
| 25 | 1.70 | 860 | 1.63 | 907 | 1.46 | 897 | 1.38 | 927 |
| 29 | 1.93 | 965 | 1.14 | 655 | 1.09 | 661 | 0.84 | 625 |
| 30 | 1.18 | 742 | 0.96 | 741 | 1.07 | 707 | 0.86 | 726 |
| 30 | 1.25 | 710 | 1.39 | 792 | 1.23 | 678 | 1.23 | 785 |
| C1 | 0.73 | 484 | 0.90 | 487 | 0.77 | 408 | 0.71 | 364 |
| C2 | 0.41 | 370 | 0.57 | 534 | 0.46 | 577 | 0.45 | 481 |
| C4 | 2.27 | 805 | 1.14 | 596 | 0.88 | 456 | 1.68 | 776 |
| C5 | 1.98 | 888 | 1.11 | 733 | 0.82 | 576 | 1.16 | 794 |

The oxygen transmission rate of the film of Example 1 was determined using test method ASTM D-3985 and an Ox-Tran ™ Twin oxygen transmission rate tester (available from MOCON, Mpls, Minn.) with a sample area of 5 cm$^2$, the relative humidity maintained at 79% and the cell temperature maintained at 25±° C. The oxygen transmission rate was determined to be 37,203 cc/m$^2$/24 hours.

We claim:

1. A transdermal drug delivery device comprising: a flexible backing and a carrier comprising a therapeutically effective amount of a drug, wherein the backing comprises a polymer blend in the form of a film about 10 to about 300 μm thick, said polymer blend comprising:
  (i) a very low density polyethylene random copolymer comprising about 80 to about 95 mole percent ethylene and a total of about 5 to about 20 mole percent of a comonomer selected from the group consisting of 1-butene, 1-hexene, 1-octene, and a combination of two or more thereof; and
  (ii) about 15 to about 600 parts by weight, based on 100 parts by weight of the very low density polyethylene, of a linear low density polyethylene random copolymer comprising about 92 to about 98 mole percent ethylene and about 2 to about 8 mole percent 1-octene;

wherein the carrier bears the backing on at least part of one surface of the carrier.

* * * * *

UNITED STATES PATENT AND TRADEMARK OFFICE
CERTIFICATE OF CORRECTION

PATENT NO. : 5,264,219
DATED : November 23, 1993
INVENTOR(S) : Godbey et al.

It is certified that error appears in the above-indentified patent and that said Letters Patent is hereby corrected as shown below:

Col. 7, Table 1, Ex 7, DFDA-1137-NT" should be --DFDA-1138-NT--.

Col. 7, Table 1, Ex C1, delete "DFDA 9063".

Col. 7, Table 1, Ex C4, "4802" should be --4803--.

Col. 9, Table 3, Ex 29, "965" should be --865--.

Col. 9, Table 3, second occurrence of Ex "30" should be --40--.

Col. 9, Table 3, Ex C1, "0.90" should be --0.80--.

Col. 10, line 3, "25±°C." should be --25±1°C.--.

Signed and Sealed this

Sixth Day of June, 1995

Attest:

BRUCE LEHMAN

Attesting Officer

Commissioner of Patents and Trademarks